(12) United States Patent
Adams et al.

(10) Patent No.: US 6,596,844 B2
(45) Date of Patent: Jul. 22, 2003

(54) CONTROLLED RELEASE POLYACRYLIC ACID GRANULES AND A PROCESS FOR PREPARING THE SAME

(75) Inventors: Daniel James Adams, Cuyahoga Falls, OH (US); David William Weaver, Avon Lake, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 10/034,011

(22) Filed: Dec. 20, 2001

(65) Prior Publication Data

US 2002/0086967 A1 Jul. 4, 2002

Related U.S. Application Data

(62) Division of application No. 09/329,471, filed on Jun. 10, 1999, now Pat. No. 6,492,488.
(60) Provisional application No. 60/095,179, filed on Aug. 2, 1998.

(51) Int. Cl.$^7$ .............................. A61K 9/28; C08Y 6/00
(52) U.S. Cl. ................ 528/502 R; 523/105; 526/307.1; 526/319; 526/318.44; 424/468; 424/469; 424/486; 424/487; 424/451
(58) Field of Search ....................... 528/502 R; 424/468, 424/469, 486, 451, 487; 523/105; 526/307.1, 319, 318.44

(56) References Cited

U.S. PATENT DOCUMENTS

| | | |
|---|---|---|
| 2,798,053 A | 7/1957 | Brown |
| 3,915,921 A | 10/1975 | Schlatzer, Jr. |
| 4,267,103 A | 5/1981 | Cohen |
| 4,386,120 A | 5/1983 | Sato et al. |
| 4,647,599 A | 3/1987 | Bezzegh et al. |
| 4,654,039 A | 3/1987 | Brandt et al. |
| 5,122,544 A | 6/1992 | Bailey et al. |
| 5,288,814 A | 2/1994 | Long, II et al. |
| 5,349,030 A | 9/1994 | Long, II et al. |
| 5,368,861 A | 11/1994 | Ushimaru et al. |

FOREIGN PATENT DOCUMENTS

| | | |
|---|---|---|
| DE | 19600324 | 7/1997 |
| WO | 9300369 | 1/1993 |
| WO | 9323457 | 11/1993 |

OTHER PUBLICATIONS

An article entitled "Compaction/Granulation of Powders Improves Solubility, Ends Dusting" reprinted from January, 1985 publication in *Food Processing* available from The Fitzpatrick Co., Elmhurst, IL.
An article entitled "Preconditioning Process Powders with Dry Granulation" reprinted from *Powder and Bulk Engineering*, Dec., 1987 and available from The Fitzpatrick Co., Elmhurst, IL.
Data WPI, Section Ch. Week 199810 Derwent Publications Ltd., London, GB; Class A14, AN 1998–109008, XP002125662 & RU2084462 C1 (Sarat Polymers Chem Techn Res Inst), (Jul. 20, 1997) abstract.

*Primary Examiner*—Tatyana Zalukaeva
(74) *Attorney, Agent, or Firm*—Thoburn T. Dunlap

(57) ABSTRACT

The present invention pertains to a method for forming poly-acrylic acid granules and granules formed therefrom wherein the granules are flowable, have an increased bulk density relative to the as polymerized polyacrylic acids, and a low amount of dust which is generally characterized herein as particles which pass through a 325 mesh screen. The granules formed by the method of the present invention can be used to prepare controlled release tablets, especially controlled release pharmaceutical tablets. The controlled release properties of the tablets formed from granules prepared according to the present invention are unexpectedly better than tablets prepared from granules formed by other known granulation methods.

7 Claims, 1 Drawing Sheet

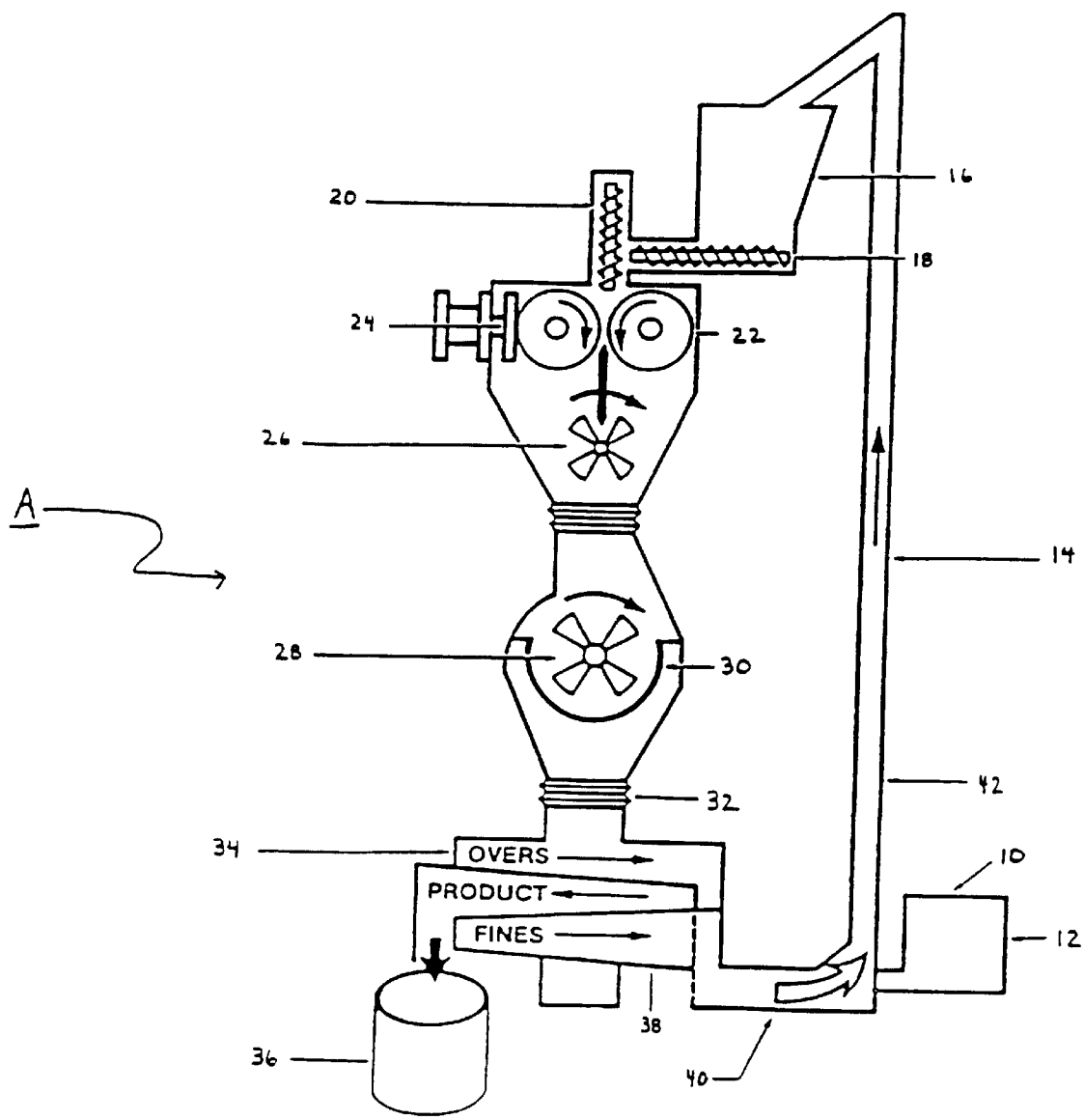
FIGURE

CONTROLLED RELEASE POLYACRYLIC ACID GRANULES AND A PROCESS FOR PREPARING THE SAME

This is a divisional of parent application Ser. No. 09/329,471 filed on Jun. 10, 1999, now U.S. Pat. No. 6,492,488, which claims the benefit of Provisional application Ser. No. 60/095,179, filed Aug. 2, 1998.

FIELD OF INVENTION

The present invention concerns a process for producing granulated polyacrylic acid. The polyacrylic polymers are highly swollen in aqueous media. The polyacrylic acid granules produced by the process of the present invention are useful in controlled release formulations (such as pharmaceutical tablets). The powdered form of polyacrylic acid, which was previously used in controlled release applications, created material handling problems due to its poor powder flow characteristics, dust, and static charges associated with the dust.

BACKGROUND OF THE INVENTION

Many compounded solids originate or are manufactured as fine, light, and/or loose powders. Such powders often have poor flow characteristics and are resistant to blending and dispersion in liquids due to clumping and poor wetting. The dust associated with the powders can exhibit static charge effects. Additional problems include difficulty in handling and, difficulty in feeding through volumetric metering equipment. Many such powders have historically been granulated to vary their particle size distribution in order to improve their characteristics. In these applications the larger granules are a temporary state with the granules being easily broken back down into the smaller powder particles by shear or solvents in the final product.

Polyacrylic acid resins, which are to be used in applications involving swelling with aqueous electrolyte solutions, are commonly polymerized in nonaqueous polymerizations where the insoluble polymer can be isolated as powders. These powders, comprised of aggregated or agglomerated polymer chains, are significantly easier to disperse and dissolve in water than the bulk polymer. However these polyacrylic acid powders have been noted for their static electricity charge, poor powder flow and some difficult in making dispersions in water since their introduction in 1958.

While some of the difficulties in using and dispersing polyacrylic acids have been addressed by various improved polyacrylic acids e.g. U.S. Pat. No. 5,349,030 and by adding components to minimize the effects of ionic charges (e.g. counterions), the problems of product dusting and poor flowability continue to be significant issues, especially with the use of very pure polyacrylic acid resins used in the pharmaceutical industry.

There are a variety of methods, which have been employed by powdered material suppliers and users in an attempt to reduce handling difficulties of powders. Slugging, hot roll milling, and fluidized bed or wet agglomeration processes are well known processes for converting powders to granules. Slugging compresses the powder into large tablets. Hot roll milling uses heat along with pressure to squeeze the powder into flakes or sheets. In either case, the compacted material is then reground into particles larger than the original powder grains. Both slugging and roll milling are relatively slow, low-capacity, energy-intensive processes. Roll milling has the additional disadvantages of requiring constant attention by a skilled operator.

Wet agglomeration techniques involve adding liquid to the original powder to increase the particle sizes and then drying the larger particles in trays or a fluidized bed. The resulting agglomerates can be used as is or ground to smaller sizes for specific uses.

Dry granulation eliminates several problems inherent in conventional processes. Dry granulation of powder material is a two-step process, requiring no heating or wetting (depending on the starting material), in which the powder is first densified (compacted) into solid form, then broken into smaller particles and separated into predetermined sizes.

To perform these steps, a granulation system combines several different kinds of specialized machines (usually in a vertical, gravity-assisted arrangement) to achieve a closed-loop operation. System components typically include: a feeding hopper, horizontal and vertical screws, compaction rollers, a prebreaker, a granulator, sizing/sorting screens, and a recycling elevator.

Granulated particles formed by the above processes are more easily handled than the powder from which they are formed. However, the granular particles may be too hard, too soft, too friable or not particularly suitable, due to the particle size distribution, for their end use (e.g. tablet forming processes).

Thus, there is a need to develop a process for preparing granulated polyacrylic acid suitable for controlled release applications e.g. pharmaceutical applications, from the polyacrylic acid powder. Desirably the process would produce granules, which retain similar properties (attributes) during formulation, forming tablets, and releasing actives from tablets to the powder without the handling problems associated with the powder.

SUMMARY OF INVENTION

The present invention pertains to a method for forming polyacrylic acid granules and granules formed therefrom wherein the granules are flowable, have comparable swelling characteristics and provide comparable tablet properties to powdered polyacrylic acid, have increased bulk density, and contain minimal amounts of very small particles that can cause dusting and/or static adherence. The granules from this process vary from other granules of similar materials in that they retain more of their dissolution and swelling characteristics in both aqueous solutions in slow release tablets than do prior art polyacrylic acid granules. The granules formed by the method of the present invention can be used to prepare controlled release tablets, especially controlled release pharmaceutical tablets where the granules have surprisingly similar characteristics during tablet formation with powders and form tablets with similar controlled release rates to tablets from the harder to handle powders. They can also be used as thickeners; emulsifiers and suspending agents in water based formulations based on other polar solvents.

Thus, a first advantage of the present invention is that polyacrylic acid powder is formulated into a granular product with better dry flow characteristics facilitating metering and mixing operations.

An additional advantage is the production of a granular polyacrylic acid having better control over particle size, higher bulk density to minimize packaging, and lower static adherence compared to unprocessed powdered polyacrylic acid.

A further advantage is that the granular polyacrylic acid produced in accordance with the present invention has relatively low dusting compared to the powder form of polyacrylic acid.

A still further advantage of the granular polyacrylic acid of the present invention is that it results in the unexpectedly better controlled release of various active material from tablets formed from the granules than from tablets formed from granules produced by other granulation processes.

The term polyacrylic acid is used to include various homopolymers and copolymers wherein at least 50 or 75 mole percent of the repeating units have pendant carboxylic acid groups or anhydrides of dicarboxylic acid groups. While acrylic acid is the most common primary monomer used to form polyacrylic acid the term is not limited thereto but includes generally all α-β unsaturated monomers with carboxylic pendant groups or anhydrides of dicarboxylic acids as described in U.S. Pat. No. 5,349,030.

Other advantages and benefits of the invention will become apparent to those skilled in the art upon a reading and understanding of the following detailed description of the preferred embodiments.

BRIEF DESCRIPTION OF THE DRAWINGS

The FIGURE shows one example of a compaction/granulation system with a recycle mechanism.

DETAILED DESCRIPTION

In accordance with the practice of the present invention, a dry granulation apparatus A is provided as shown in the Figure. Variables such as the compaction pressure, roll speeds, attrition device and operation speed, and screening operations are used to control the particle densification and particle size distribution. These properties control the dissolution behavior of the polyacrylic acid when exposed to water or electrolyte solutions and its effectiveness as an additive in tablet formulations and controlled release applications.

Referring now to the FIGURE, the dry granulator A is provided with an original powder feed 10 which feeds powdered polyacrylic acid into a lower hopper 12. The powdered acrylic acid in lower hopper 12 is then fed through feed channel 14 into an upper hopper 16. The upper hopper 16 collects the virgin powdered polyacrylic acid and recycled powder which does not meet quality controlled sizing parameters. The powdered acrylic acid in the upper hopper is then initially fed into the granulation system via a horizontal feed screw 18. The rate of rotation of the horizontal feed screw 18 can be adjusted to permit continuous flow of the powdered polyacrylic acid into the granulation system without clogging. Next, a vertical screw 20 precompresses and deaerates the powered polyacrylic acid before feeding it into compaction rollers 22. Pressure is applied to compaction rollers 22 via a hydraulic actuator 24. The compaction rollers rotate in opposite directions so that powdered material fed from above will be pulled between the rollers, compressed and dropped into a prebreak mechanism 26 below. The prebreak mechanism 26 provides an initial breakup of the compressed polyacrylic acid into chips and flakes, which drop into attritor 28. The attritor 28 breaks up the compressed polyacrylic acid into desired particle sizes in conjunction with screen 30. Granulated polyacrylic acid falls into a screening system 32 wherein particles are separated via various sieves 34, the final product having the desired particle sizes being deposited into finished product hopper 36. The oversized and undersized particles 38 are processed via a recycle feed mechanism 40 back into feed channel 14, 42 to be reprocessed through the system.

Various powdered polyacrylic acids, or mixtures of polyacrylic acids, may be granulated according to the process of the present invention wherein the resulting granulated polyacrylic acid has enhanced handling and performance properties compared to the powder. The granulated polyacrylic acid prepared in accordance with the method described herein, when formulated into tablets retains an ability to slow down the release rate of an active material, compared to tablets formed from granules prepared by other known granulation processes. The granules also maintain more of their ability to thicken, emulsify, and suspend in water based formulations and formulations based on other polar solvents than prior art granules.

Polymeric powders which may be formed into granules that have improved handling, while retaining thickening and controlled release properties, include various acrylic acid homopolymers, copolymers, and interpolymers having a bulk density below about 0.3 g/cc. The term polyacrylic acid or acrylic acid polymers is used to encompass a variety of polymers having high percentages of polymerizable monomers therein with pendant carboxylic acid groups or anhydrides of polycarboxylic acid. These are described in more detail in U.S. Pat. Nos. 2,798,053; 3,915,921; 4,267,103; 5,288,814; and 5,349,030 hereby incorporated by reference. The term polyacrylic acid is used to include various homopolymers, copolymers, and interpolymers, wherein at least 50 or 75 mole percent of the repeating units have pendant carboxylic acid groups or anhydrides of dicarboxylic acid groups. While acrylic acid is the most common primary monomer used to form polyacrylic acid the term is not limited thereto but includes generally all α-β unsaturated monomers with carboxylic pendant groups or anhydrides of dicarboxylic acids as described in U.S. Pat. No. 5,349,030. The term consisting essentially of anhydrous polyacrylic acid will be used to exclude more than 3 weight percent water and to exclude more than 0.2 mole percent multivalent metal cations based on the moles of carboxylic acid. Desirably, the amount of water is less than 1 or 2 weight percent. Desirably, the amount of multivalent metal cations is less than 0.1 mole percent and preferably less than 0.01 mole percent.

In particular, the process according to the present inventions is useful for granulating various powdered polycarboxylic acids including cross-linked polyacrylic acids. Specific types of cross-linked polyacrylic acids include Carbopol® 971P (polymerized in ethyl-acetate and partially neutralized with potassium); copolymers of acrylic acid and alkyl acrylates; copolymers of acrylic acid and alkyl vinyl ethers; copolymers of ethylene and maleic anhydride; and copolymers of maleic anhydride and alkyl vinyl ethers. An approved polyacrylic acid for pharmaceutical applications, described in a carbomer monograph in the U.S. Pharmocopia 23 NR 18, is a polyacrylic acid crosslinked with polyalkenyl ethers. The polymeric agents useable in the present invention are typically polymerized by precipitation polymerization in a non-aqueous medium and subsequently dried to strip off the solvent. The acrylic polymers typically have a flow index of above 30, apparently due to their low bulk density and electrostatic charge.

The acrylic polymers of interest when dispersed in water and neutralized to a pH of 7 at a concentration of 10 g/L generally can impart a viscosity of at least 500 centipoise and more desirably at least 2000 centipoise to the water solution as measured by a Brookfield viscometer using 20 rpm at 25° C. and selecting a spindle resulting in a torque reading between 10 and 90% of full scale.

The improved handling properties of the granules prepared in accordance with the present invention are reflected by improvements over the powdered form of polyacrylic acid in areas such as powder flow rate, bulk density, percentage of fines (i.e. particles less than 325 U.S. Standard screen size), static adherence and total dust.

The granulated product desirably retains the at least 70, 80 or 90% of the thickening capacity of the original fine powder when dispersed in water and neutralized to a pH of 7 at a concentration of 10 g/L. Thus the viscosity of such a solution is desirably at least 350, 400, or 450 centipoise and more desirably at least 1400, 1600 or 1800 centipoise.

With respect to powder flow rate, the granules according to the present invention may have a flow index value of less than or equal to 25, desirably less than or equal to 20, and preferably less than or equal to 15. The flow index is measure by the Flodex™ equipment, which comprises a 35–45 mm diameter tube approximately 8–10 cm long. Bottom caps with incrementally larger diameter apertures are used in the apparatus until an aperture is found of sufficient diameter that the contents of the tube are substantially emptied from the tube when the aperture is unblocked by the operator. A flow index value is assigned equal to the diameter of the aperture used in mm through which the material flows easily. If the aperture is too small then bridging over occurs with a substantial amount of the tube contents being retained in the tube.

The bulk density of the granules is measured according to a typical bulk density method for powders. A 30–100 mL cup is used which can be lightly tapped one time after filling. The powder is dropped from a powder funnel which discharges about 4 to 8 cm above the rim of the cup. The excess material which accumulates above the rim of the cup can be removed by scraping with a spatula and the weight of the contents determined. The bulk density is the weight of the contents divided by their volume. A tap density can also be determined using a 100 mL graduated cylinder instead of a cup. The powder is discharged from the bottom of a powder funnel as set forth above. A tap density apparatus such as a J. Engelsmann A-G Tap Density Apparatus is used to tap the cylinder and contents 1000 times. The volume and weight of the powder after tapping is recorded and the density is calculated as the weight divided by the volume.

Due to the propensity of very small particles to cause dusting, it is desirable to screen the granules to remove and recycle those granules which pass through a 325 U.S. Standard mesh screen. This is not to say that particles smaller than a 325 mesh screen are dust but rather that this size fraction includes more dust and/or carries more dust with it into other steps. Desirably the amount of granules that pass through said 325 mesh screen are less than 10 weight percent of the total granules, more desirably less than 5 weight percent, and preferably less than 2 weight percent of the granulated product after screening. The amount of granules passing through a 325 mesh screen can be determined by screening the granules until the weight of the material passing through the 325 mesh screen appears to be constant. If a screen analysis on the polyacrylic powder (before granulation) is desired, small sample sizes or air filtration techniques are recommended due to the substantial amount of very small particles in the powder and static charge problems that occur during screening.

Static charging for polyacrylic acid is generally visually determined. Powder samples in bags will exhibit a strong tendency for dust to adhere to the bag and any equipment and/or the operator. Samples of polyacrylic acid powder in glass and plastic jars (generally nonconductive) will exhibit large amounts of dust adhered by static electricity to the walls of the jar above the samples. Static charged dust particles will appear to exit the glass jar as a smoke due to static repulsion combined with Browman particle diffusion.

In order to achieve production of polyacrylic acid granules, which possess both the improved handling properties over the powder and retain acceptable tablet formation and controlled release properties compared to the powder, a number of adjustable parameters must be controlled. These parameters include horizontal feed screw rate of rotation, vertical screw rotation speed, pressure applied to compaction rolls, speed of compaction rolls, attritor configuration and speed, and screen size.

The speeds of the horizontal and vertical screws should be set to feed powder to the compaction rollers at a rate just fast enough to cause a slight separation (about 0.01 to about 0.2 or 0.5 inches, more desirably from about 0.02 to about 0.07 or 0.2 inch gap) between the rollers.

Pressure is applied to the compaction rollers via the hydraulic actuator or other compaction device to produce a compacted material having a density of about 0.3 g/cc to about 1.5 g/cc. Preferably, the density of the compacted material is from about 0.9 g/cc to about 1.1 g/cc. These densities form strong enough aggregates and/or agglomerates that the amounts of undersized particles can be reduced without removing so much of the voids, cracks, and crevices (void volume) within the aggregates and agglomerates to prevent them uniformly swelling in water or electrolyte solutions. The compaction rolls may have circumferiential corrugations, pocket indentations or corrugations in the axial direction across the width of the roll. Applicants define the pressure via the result due to the complexity of specifying a compaction pressure applied from a curved surface to a powder.

Densification obviously is the result of compacting the aggregates and/or agglomerates (particles) present in the powder into larger particles. This reduces the void volume within the particles. It is believed that the void volume, to the extent that it is open to the surface of the particles, is a pathway for water or electrolyte solutions to enter each particle uniformly swelling the polyacrylic acid therein. Thus densification usually makes the interior of the particles less accessible to water or electrolyte solutions.

Increased compaction also results in more interpolymer penetration between the surface polymers on aggregates and/or agglomerates, which can slow dissolution times of a particle due to the need for the interpenetrated polymers to separate and due to the possibility that the interpenetrated polymers may remain entangled and not be able to separate. It is to be noted that if the polyacrylic acid is over-densified then the resulting granules will only swell with water or electrolyte on their surfaces. This results in occlusions of nonswollen polymer (occluded polymer) within some or all granules.

The occluded (non-swellable) polyacrylic acid is not available to modify the viscosity of liquid solutions and is not available to control release rates in a tablet. Therefore there is an inverse relationship between the amount of occluded polyacrylic acid and the thickening and release controlling properties of the polyacrylic acid.

The compaction roller speed is set to maximize productivity without exceeding the horsepower limitation of the compaction equipment. Slower roller speeds allow the polyacrylic acid more time to flow and accommodate the stresses uniformly throughout the thickness of the compressed samples. Faster roller speeds may force the polyacrylic acid in direct contact with the roller surface to do most of the accommodation.

The speed and configuration of the attritor are chosen to provide optimal particle size distributions for a particular application. Smaller particles, such as those sized between the opening of a 100 and 200 mesh screen are desirable as they maximize the number of particles and total surface area. These properties are important, as smaller polyacrylic acid particles tend to form a tablet with better integrity and slower release rates for active material. Increases in the number of smaller particles decreases bulk density and decrease powder flow characteristics. It has also been observed that smaller particles form tablets with better tablet integrity in the dissolution tests. Larger particles, e.g. those sized between a 20 and 80 mesh screen, maximize bulk density and flow characteristics but contribute less to tablet formation and slow release rates. In most embodiments it is desirable to minimize generation of granules smaller than 325 mesh, more desirable less than 200 mesh (U.S. Standard) due to their contribution to dust.

Screen size is about 5 mesh to about 325 mesh (U.S. Standard); more desirably from about 20 to about 250, and preferably, screen size is from about 40 mesh to about 200 mesh. Thus, granules having a particle size of less than about 5 mesh (passing through 5 mesh) but greater than about 325 mesh (retained on 325 mesh) will be discharged as product. Particles which have sizes outside these parameters (oversized and undersized (fines)) will desirably be recycled back into the system if present in a significant amount.

Vacuum deaeration may be used to reduce air from becoming trapped in the powder prior to compaction. The vacuum may be adjusted to be from about 0.5 in. Hg. to about 30 in. Hg. Preferably 5 to 20. Desirably this vacuum is applied around the compaction rolls and optionally within the vertical and/or horizontal screw feeds. If alternative compaction or powder conveyance means are used they could include vacuum deaeration. Entrained air in the material from the initial compaction tends to expand uncontrollably as the compacted material comes out of the compaction rolls and fracture the compacted material.

The controlled release tablet formulations of the present invention include granulated polyacrylic acid prepared in accordance with the process of the invention. Amounts of polyacrylic acid used in tablet formulations are preferably from about 5 or 10% w/w to about 50% w/w. The polyacrylic acid aids in tablet formation and tablet integrity. During controlled release applications the polyacrylic acid can swell which limits the porosity of the tablet (or application device) by restricting the flow of the electrolyte solution into and out of the tablet. Desirably the tablets made according to this disclosure have a release rate of from about 0.6 to about 24 hours or more for pharmaceutically active materials. Longer release rates are available for non-pharmaceutical applications where the longer release rates may be desirable.

Other conventional tableting adjuvants, including pharmaceutically acceptable tableting adjuvants, can be included in the tablet formulations. Such adjuvants include fillers, excipients, compression aids, binders, flavorings, coating agents, etc.

Various active materials, e.g. pharmaceuticals, may be formulated into the controlled release tablet formulations. Other active materials include biocides, disinfectants, stimulants, moisturizers, aromas, scents, chemicals (e.g. chlorine), proteins, etc which are beneficially applied from a table or gelled or thickened liquid formulation. Typically, pharmaceuticals dosages are designed to be administered in specific amounts over a broad time range to avoid toxicity problems, thus the need for controlled release formulations. Pharmaceutical can include pain relievers, stimulants, muscle relaxants, antibiotics, pain blockers, and a variety of other medications. Theophylline, for example, is one such agent, which is generally formulated in a controlled release tablet composition. Other pharmaceutical agents typically or desirably used in controlled release form are within the scope of acceptable pharmaceutical agents useable in the present invention's formulations.

PREPARATION EXAMPLES

The following examples illustrate the processes for preparing polyacrylic acid granules, which possess the desired handling and controlled release properties.

Preparation Examples 1 and 2

The following examples utilized a Fitzpatrick Model 4L×10D Chilsonator and DKAS012 FitzMill system. This equipment is illustrated in FIG. 1. The Fitzpatrick Company has a compaction division in Elmhurst, Ill., which sells this type of equipment. Another supplier of similar equipment is Alexanderwerk based in Germany and having a sales office in New Jersey. The Chilsonator used two 4" long rolls having diameters of 10". Vacuum was applied in the area of the vertical screw. The material granulated was Carbopol® 971P, a lightly crosslinked polyacrylic acid powder.

TABLE I

|  | Example 1 | Example 2 |
|---|---|---|
| Feed (lbs/hr.) | 360 | 390 |
| Roll Pressure (psig) | 800 | 1000 |
| Roll Speed (RPM) | 12 | 12 |
| Vacuum (in. Hg.) | 7 | 7 |
| Granulator Speed (RPM) | 1250 | 1250 |
| Screen size/type | 0.079/Rasping | .079/Rasping |
| Sieve Size (mesh) | 10–84 | 10–84 |
| % Product | 82 | 85 |
| wt. % Overs/wt. % Fines | 1.8/16 | 1.6/14 |

TABLE Ia

|  | Powder | Example 1 (From Table I) | Example 2 (From Table I) |
|---|---|---|---|
| $T_{70}SGF^*$ (minutes) | 482 | 310 | 244 |
| $T_{70}SIF^*$ (minutes) | 627 | 347 | 274 |

*SGF = Simulated Gastric Fluid (pH 1.2); SIF = Simulated Intestinal Fluid (pH 6.8); $T_{70}$ is time (in minutes) for 70% of the active ingredient (theophylline) to be released in SGF or SIF.

Tables I and Ia show that drug release time can be adjusted by manipulating roll compaction pressure. The tablet from Table Ia release rate tests was formulated with a similar recipe to Table III, and compacted with sufficient pressure to result in a tablet with a hardness of 9–11 kilopounds using a standard U.S.P. crushing strength tester.

TABLE Ib

Viscosities of Aqueous Dispersions at Various Resin Concentrations
(Neutralized to about pH 7.5 with NaOH)

|  | Powder | Example 1 (from Table I) | Example 2 (From Table I) |
|---|---|---|---|
| 0.2% Resin | 3250 | 2930 | 2810 |
| 0.5% Resin | 6050 | 5750 | 5700 |
| 1.0% Resin | 9850 | 9300 | 9300 |
| 1.0% Resin + 1.0% NaCl | 3070 | 2700 | 2680 |

Viscosities measured with Brookfield viscometer, 20 rpm, 25 C using a spindle for which the total torque is 10 to 90% of full scale on the torque meter.

Tables I and Ib show how thickening ability decreases only slightly with increasing compaction pressure. However, it should be noted that the gel surface may appear rougher with increasing compaction pressure.

Formulation Examples

The following examples illustrate the physical characteristics of granules produced according to the present invention. The samples were prepared using a Fitzpatrick IR-520 Chilsonator roll compactor and a M5A Fitzmill attritor. Carbopol®971P was used in the following examples.

TABLE II

| Formulation Example # | Roll Speed/ Pressure (RPM) | Flow −20 mesh* | Flow 20–80* |
|---|---|---|---|
| 1 | 5/1,000 | 22 | 18 |
| 2 | 10/700 | 32 | 24 |
| 3 (Control-powder) | — | 34 | n/a |
| 4** (comparative Example) | n/a | 22 | 22 |

*Smallest hole diameter (mm.) in Flodex ™ through which material flows easily.
**Prepared by fluidized bed wet granulation with water.

The following Examples illustrate pharmaceutical tablet formulations comprising theophylline. Examples 1 and 2 utilize Carbopol granules from Table II above. Comparative examples include powdered polyacrylic acid and polyacrylic acid granules produced by fluidized bed granulation. All amounts used in % w/w.

TABLE III

|  | Ex. 1 | Ex. 2 | Ex. 3 (powder) | Ex. 4 |
|---|---|---|---|---|
| Theophylline | 33.3 | 33.3 | 33.3 | 33.3 |
| Anhydrous Lactose | 45.7 | 45.7 | 45.7 | 45.7 |
| Carbopol ®971P (as is or granulated) | 20.0 | 20.0 | 20.0 | 20.0 |
| Cab-O-Sil | 0.5 | 0.5 | 0.5 | 0.5 |
| Magnesium Stearate | 0.5 | 0.5 | 0.5 | 0.5 |

*fluidized bed granulation.

Table IV, below, shows properties of powder mixtures and tablets formed from granules prepared according to the present invention compared to powder mixtures and tablets formed from either powdered polyacrylic acid (Ex. 3) or granules produced via the fluidized bed technique (Ex. 4).

TABLE IV

|  | Ex. 1 | Ex. 2 | Ex. 3 (powder) | Ex. 4* (comparative) |
|---|---|---|---|---|
| Flodex (flow index) (before tableting) | 32 | 26 | 32 | >32 |
| Compressibility Index (before tabletting) | 22.9 | 18.8 | 21.8 | 28.5 |
| $T_{70}$** SGF/SIF*** | 100/573.58 | 162/623 | 466/1006 | 62/66 |
| $T_{90}$** SGF/SIF*** (minutes) | 122/663 | 210/725 | 673/1343 | 71.6/(<90) |

*granules produced by fluidized bed technique
**$T_{70}$ and $T_{90}$ are time (in minutes) for 70% and 90% of active ingredient (theophylline) to be released in SGF/SIF.
***SGF (pH 1.2) = Simulated Gastric Fluid; SIF (pH 6.8) = Simulated Intestinal Fluid.

Table IV shows that the flowability (flow-index) of the tableting powder mixture prepared from various granular forms of polyacrylic acid is not fundamentally related to the drug release performance of the granules. The compressibility index is 100 times the difference between the tap density and bulk density divided by the tap density. In free flowing powders, the compressibility index is less than 15% while values above 25% indicate poor flow characteristics.

The following Tables V–VII illustrate the dramatic effect of compression pressure during compaction of the polyacrylic acid granules on the properties of the tablet blends when using the polyacrylic acid as a 10 weight percent ingredient. The polyacrylic acid of Example 5 was compacted under a pressure of 10 bar on an Alexanderwerk granulating machine, Example 6 was compacted under a pressure of 30 bar, and Example 7 was compacted under a pressure of 60 bar.

TABLE V

| Composition | Ex. 5 | Ex. 6 | Ex. 7 |
|---|---|---|---|
| Theophylline | 32.9 g | 32.9 | 32.9 |
| Anhydrous lactose | 55.7 | 55.7 | 55.7 |
| Polyacrylic acid | 10 | 10 | 10 |
| Compaction pressure for polyacrylic acid (bar) | 10 | 30 | 60 |
| Cabosil (fumed silica) | 0.4 | 0.4 | 0.4 |
| Magnesium stearate | 1.0 | 1.0 | 1.0 |

TABLE VI

Properties of Tablet Blend

| Properties | Ex. 5 | Ex. 6 | Ex. 7 |
|---|---|---|---|
| Bulk density | .0566 | 0.404 | 0.476 |
| Tap Density | 0.765 | 0.475 | 0.560 |
| Hausner Ratio | 1.352 | 1.175 | 1.176 |
| Compressibility Index % | 26.01 | 14.95 | 15.00 |

The tablet blends in Table V were formed in a 0.375-inch diameter die with a blend loading of 300 mg for each of Examples 5–7. The force used for Examples 5 was 300 lbs, that for Example 6 was 364 lbs, and that for Examples 7 was 367 lbs. These values were calculated based on the Hausner Ratio and the Compressibility Index of the tablet blend. The Hausner ratio is the tap density divided by the bulk density.

It is to be noted that the hardness of the tablets from Examples 5–7 were 8.7, 8.8, and 8.4 lbs indicating that Examples 6 and 7 were not compressed into harder tablets than Example 5.

TABLE VII

Properties of Tablet

|  | Ex. 5 | Ex. 6 | Ex. 7 |
|---|---|---|---|
| Release in SGF T20 | 60 | 52 | 39 |
| T50 | 279 | 152 | 70 |
| T70 | 445 | 196 | 81 |
| T90 | 764 | 316 | 92 |
| Release in SIF T20 | 174 | 184 | 153 |
| T50 | 702 | 592 | 460 |
| T70 | 1133 | 828 | 627 |
| T90 | — | 1173 | 712 |
| Dissolution Time (min) | 34.9 | 33.5 | 36.0 |
| Tablet thickness (inch) | 0.1748 | 0.1728 | 0.1755 |

The above Table VI illustrates what a dramatic effect 10 weight percent of polyacrylic acid, granulated under different conditions, can have on the properties of blends used to make tablets and Table VII illustrates the dramatic effect on the release rate of theophylline. As is well known to the pharmaceutical industry, theophylline is a very effective medication, but it can be toxic if released in concentrations above the pharmaceutically effective amounts. Therefore uniform and controlled safe dosages of theophylline are critical in preparing effective tablets. In Table VI the blend before tablet making from the polyacrylic acid compacted under the lowest compaction pressure resulted in the densest blend with the highest compressibility (facilitating tablet formation at lower pressures). When these blends were compressed into tablets the compaction pressures used to form granules of polyacrylic acid had little effect on the disintegration times. The release time of theophylline by the tablets was dramatically decreased by increasing compaction roll pressure.

Results

As can be seen from the tables above, granules produced in accordance with the present invention have enhanced flowability compared to the control powder (Table II). Additionally, Table II shows the importance of screening out fines to achieve increased flowability.

In addition to enhanced flowability, tablets prepared from granules of polyacrylic acid made in accordance with the process of the present invention possess enhanced (slowed down) controlled release properties over granules of polyacrylic acid prepared by other known granulation processes (i.e., fluidized bed). While the controlled release properties of tablets prepared from granulated polyacrylic acid according to the present invention are not quite as slow as tablets prepared from powdered polyacrylic acid, the undesirable handling properties of prior art powders are avoided as the granules have improved flowability, lower static adherence and lower dust compared to the powdered polyacrylic acid itself. These major advantages in pretableting handling characteristics more than compensate for the somewhat lowered thickening efficiency or slight changes in the controlled release properties.

While in accordance with the patent statutes the best mode and preferred embodiment has been set forth, the scope of the invention is not limited thereto, but rather by the scope of the attached

What is claimed is:

1. A process for granulating polyacrylic acid such that the granulated polyacrylic acid has the following properties:

(i) a flow index of $\leq 25$, (ii) a bulk density of at least 0.35 g/cc, and (ii) less than 5 wt. % particles are fine enough to pass through a U.S. Standard 325 mesh screen, said process comprising:

(a) delivering a fine powder consisting essentially of anhydrous polyacrylic acid to a compaction device;

(b) compacting said polyacrylic acid into larger agglomerates and/or aggregates, (c) fracturing said agglomerates and/or aggregates into smaller granules;

(d) optionally screening said smaller granules to obtain the desired particle size range by removing or recycling in said process oversized and/or undersized granules, said polyacrylic acid being a polymer of one or more monomers characterized by having at least 50 mole percent repeating units having a carboxylic acid group and/or an anhydride of a dicarboxylic acid and when dispersed in water and neutralized to a pH of 7 at a concentration of 10 g/L imparting a viscosity of at least 500 centipoise to said water.

2. The process of claim 1 wherein said compacting of said polyacrylic acid is achieved by the use of compaction rollers.

3. The method of claim 2 wherein said compacting rollers are adjusted to a separation between the roller of from about 0.01 to about 0.5 inches.

4. The method of claim 3, wherein the pressure on said rollers is sufficient to form a coherent strip from the compaction rollers.

5. The method of claim 1 wherein the polyacrylic acid is a cross linked polyacrylic acid.

6. The method of claim 1 wherein the fine powder, optionally with undersized and/or oversized granules, is delivered to said compaction device via one or more vertical and/or horizontal screws.

7. The method of claim 1 wherein the granules produced have an average particle size of between 5 and 325 U.S. Standard mesh screen.

* * * * *